(12) United States Patent
Saito et al.

(10) Patent No.: US 9,034,463 B2
(45) Date of Patent: May 19, 2015

(54) BNA CRYSTAL

(75) Inventors: Mikiko Saito, Wako (JP); Takashi Notake, Wako (JP); Hiroaki Minamide, Wako (JP); Hiromasa Ito, Wako (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 13/807,187

(22) PCT Filed: Jun. 10, 2011

(86) PCT No.: PCT/JP2011/063311
§ 371 (c)(1),
(2), (4) Date: Dec. 27, 2012

(87) PCT Pub. No.: WO2012/002130
PCT Pub. Date: Jan. 5, 2012

(65) Prior Publication Data
US 2013/0108853 A1 May 2, 2013

(30) Foreign Application Priority Data

Jun. 29, 2010 (JP) ................. 2010-148073

(51) Int. Cl.
| C30B 29/54 | (2006.01) |
| C07C 205/06 | (2006.01) |
| C30B 7/08 | (2006.01) |
| C30B 7/00 | (2006.01) |
| C07C 211/52 | (2006.01) |
| G02F 1/355 | (2006.01) |

(52) U.S. Cl.
CPC ... *C30B 7/08* (2013.01); *C30B 7/00* (2013.01); *C30B 7/005* (2013.01); *C07B 2200/13* (2013.01); *C07C 211/52* (2013.01); *C30B 29/54* (2013.01); *G02F 1/3551* (2013.01)

(58) Field of Classification Search
None
See application file for complete search history.

(56) References Cited

U.S. PATENT DOCUMENTS 7,081,984 B1 * 7/2006 Bahra et al. .................. 359/328

FOREIGN PATENT DOCUMENTS

| JP | H06-087685 A | 3/1994 |
| JP | 2000-256100 A | 9/2000 |
| JP | 2001-247400 A | 9/2001 |

OTHER PUBLICATIONS

M.D. Aggarwal, J. CHoi, W.S. Wang, K. Bhat, R.B. Lal, Angela D. Shields, Benamin G. Penn, Donald O. Frazier; "Solution growth of a novel nonlinear optical material: L-histidine tetrafluoroborate". Journal of Crystal Growth 204 (1999) 179-182.*
C. Owens, K. Bhat, W.S. Wang, A. Tan, M.D. Aggarwal, Benjamin G. Penn, Donald O. Frazier; "Bulk growth of high quality nonlinear optical crystals of L-arginine tetrafuoroborate (L-AFB)". Journal of Crystal Growth 225 (2001) 465-469.*

(Continued)

*Primary Examiner* — David Sample
*Assistant Examiner* — Donald M Flores, Jr.
(74) *Attorney, Agent, or Firm* — Leydig, Voit & Mayer, Ltd.

(57) ABSTRACT

An object of the present invention is to produce a non-conventional high-quality BNA single crystal. Another object of the present invention is to provide a process for producing the above-described high-quality BNA single crystal. Specifically, the present invention provides a BNA crystal characterized by having a half-value width of diffraction peak X-ray intensity of 100 seconds or less in a rocking curve measurement by X-ray diffraction method.

5 Claims, 3 Drawing Sheets

(56) References Cited

OTHER PUBLICATIONS

H. Hashimoto, Y. Okada, H. Fujimura, M. Morioka, O. Sugihara, N. Okamoto, R. Matsushima, "Second-Harmonic Generataion from Single Crystals of N-Substituted 4-Nitroanilines"; Jpn. J. Appl. Phys., vol. 36 (1997), pp. 6754-6760.*

K. Miyamoto, S. Ohno, M. Fujiwara, H. Minamide, H. Hashimoto, H. Ito, "Optimized terahertz-wave generation using BNA-DFG"; Opt. Express, vol. 17, No. 17 (Aug. 17, 2009), p. 14832-14838.*

K. Kawase, T. Hatanaka, H. Takahashi, K. Nakamura, T. Taniuchi, H. Ito, "Tunable terahertz-wave generation from DAST crystal by dual signal-wave parametric oscillation of periodically poled lithium niobate"; Opt. Lett., vol. 25, No. 23 (Dec. 1, 2000), p. 1714-1714.*

K. Miyamoto, H. Minamide, M. Fujiwara, H. Hashimoto, H. Ito, "Coherent tunable monochromoatic Terahertz-wave generation using N-Benzyl-2-methyl-4-nitroaniline (BNA) crystal"; Proc. of SPIE, vol. 6875 (2008), p. 68750C-1 to 68750C-8.*

Fujiwara et al., *Japanese Journal of Applied Physics*, 45(11): 8676-8685 (2006).

Fujiwara et al., *Japanese Journal of Applied Physics*, 46(4A): 1528-1530 (2007).

Kuroyanagi et al., *Japanese Journal of Applied Physics* 45(29): L761-L764 (2006).

Notake et al., *Proceedings of 57th Meeting of the Japan Society of Applied Physics and Related Societies*, 19p-L-8 (Mar. 3, 2010).

International Bureau of WIPO, International Preliminary Report on Patentability in International Patent Application PCT/JP2011/063311(Feb. 21, 2013).

Japanese Patent Office, International Search Report in International Patent Application No. PCT/JP2011/063311 (Aug. 16, 2011).

Hashimoto et al., *Japanese Journal of Applied Physics*, 36(11): 6754-6760 (1997).

Kuroyanagi et al., *Japanese Journal of Applied Physics*, 45(5A): 4068-4073 (2006).

Miyamoto et al., *Proc. of SPIE*, 6875: 68750C [doi: 10.1117/12.762620] (2008).

Notake et al., "Solution growth of an organic N-benzyl-2-methyl-4-nitroaniline (BNA) crystal for DFG-THz source," *35th International Conference on Infrared Millimeter and Terahertz Waves (IRMMW-THZ)*, pp. 1-2 (Sep. 5, 2010).

Notake et al., "Hybrid Terahertz-Wave Source with Ultrawideband Tunability utilizing Organic DAST and BNA Crystals," *2011 Conference on Lasers and Electro-Optics (CLEO), Laser Science to Photonic Applications*, pp. 1-2 (May 1, 2011).

Vijay et al., *Journal of Crystal Growth*, 312(3): 420-425 (2010).

European Patent Office, Extended European Search Report in European Patent Application No. 11800598.2 (Dec. 5, 2013).

* cited by examiner

BNA CRYSTAL

CROSS-REFERENCE TO RELATED APPLICATIONS

This patent application is the U.S. national phase of International Patent Application No. PCT/JP2011/063311, filed on Jun. 10, 2011, which claims the benefit of Japanese Patent Application No. 2010-148073, filed Jun. 29, 2010, the disclosures of which are hereby incorporated by reference in their entireties.

TECHNICAL FIELD

The present invention relates to a crystal of N-benzyl-2-methyl-4-nitroaniline (hereinafter also referred to as BNA) which is an organic nonlinear optical crystal, and a process for producing the same.

BACKGROUND ART

For application in high-power terahertz-wave generation, efficient wavelength conversion, ultra-high-speed light modulation device, and the like, organic materials having high nonlinear susceptibility and ultra-high-speed response which is said to be subpicosecond have been actively developed. With respect to an organic material 4-dimethylamino-N-methyl-4-stilbazolium tosylate (hereinafter also referred to as DAST), high-quality single crystallization techniques have been developed, and processes for producing the same have been proposed (see Patent Documents 1 and 2).

The DAST described above has high nonlinearity but is deliquescent, thus being problematic from the standpoint of processing or durability of a crystal. Specifically, because of the deliquescence, the DAST cannot be processed by normal optical polishing using water and abrasive grains; in addition, it deteriorates over time because it absorbs water vapor in the atmosphere, thus there have been difficulties in industrial applications.

On the other hand, BNA which is a novel organic nonlinear optical crystal, despite having nonlinear polarizability as high as that of the DAST described above, is not deliquescent and chemically stable, is easily subjected to optical polishing/processing, and shows excellent temporal stability even after use/storage in a normal environment. Thus, when considering industrial applications as a monochromatic terahertz wave-generating element or an optical device having broadband wavelength tunability in the future, BNA is a useful nonlinear optical crystal.

Regarding such a BNA crystal, it has been reported that the vertical Bridgman method was used to attempt single crystal growth from a melt to obtain a BNA crystal with a practical size (8×10 mm) (Non-Patent Document 1). Further, it has also been reported that the refractive index, absorption coefficient, and the like of the BNA single crystal described above were determined (Non-Patent Documents 2 and 3).

PRIOR ART DOCUMENTS

Patent Documents

Patent Document 1: JP 2000-256100 A
Patent Document 2: JP 2001-247400 A

Non-Patent Documents

Non-Patent Document 1: "Second Order Nonliner Optical Properties of the Single Crystal of N-Benzyl 2-methyl-4-nitroaniline: Anomalous Enhancement of the d333 Component and Its Possible Origin" M. Fujiwara, etc. Japanese Journal of Applied Physics, Vol 45, No. 11, 8676-8685 (2006)

Non-Patent Document 2: "Determination of Refractive Indices and Absorption Coefficients of Highly Purified N-Benzyl 2-methyl-4-nitroaniline Crystal in Terahertz Frequency Regime" K. Kuroyanagi, etc. Japanese Journal of Applied Physics, Vol 45, No. 29, L761-L764 (2006)

Non-Patent Document 3: "Determination of the d-Tensor Compounds of a Single Crystal of N-Benzyl 2-methyl-4-nitroaniline" M. Fujiwara, etc. Japanese Journal of Applied Physics, Vol 46, No. 4A, 1528-1530 (2007)

SUMMARY OF THE INVENTION

Problems to be Solved by the Invention

As a method for producing a BNA crystal reported in the above Non-Patent Documents, the vertical Bridgman method which is one of the melt methods are employed. Techniques for growing a crystal from a melt such as the vertical Bridgman method have the advantage that a large single crystal can be grown, but on the other hand require a large temperature gradient at a growth interface in order to crystallize a melt and also undergo mechanical stress caused by the difference in thermal expansion between a crystal and an ampule for containing it. As a result, lattice distortion is likely to occur in the crystals, and defect density tends to be high. The BNA crystals that have been reported at present have a problem of a low damage threshold for pump light because of their insufficient quality.

In addition, regarding equipment necessary for crystal growth, when the crystal growing technique using the vertical Bridgman method is employed, it has been necessary to construct large and complex equipment; for example, a high-temperature heating system for melting raw materials is required; necessity for a furnace for providing a temperature gradient; and, in addition, a sealed tube must be used when materials have a high vapor pressure.

Means for Solving the Problems

The present inventors intensively studied to solve the above problems and employed a method different from the melt methods such as the vertical Bridgman method described above to improve the crystal grow method, thereby successfully producing a non-conventional and high-quality BNA single crystal, thereby completing the present invention. The present invention is a BNA crystal characterized by having a half-value width of diffraction peak X-ray intensity of 100 seconds or less in a rocking curve measurement by X-ray diffraction method.

Further, being produced by the solution method is a preferred aspect, and having a long side/short side length of 5 mm or more and a thickness of 0.5 mm or more is a preferred aspect.

Further, another aspect of the present invention is a process for producing a BNA crystal by the solution method, comprising the step of obtaining a seed crystal and the growth step in which the seed crystal obtained is grown in a solution, wherein, in the above-described crystal growth step, the above-described seed crystal is held by a crystal holding part and held at an end in the main growth direction of the seed crystal by the above-described holding part; and the solution used in the above-described crystal growth step is a supernatant solution after precipitation of the seed crystal in the above-described step of obtaining a seed crystal.

Further, precipitating and growing the crystal by slowly cooling the solution in the above-described step of obtaining a seed crystal and the above-described growth step is a preferred aspect.

Effects of the Invention

By the present invention, a BNA crystal with remarkably superior crystal quality to that of the hitherto reported BNA crystals produced by the melt method can be provided. Accordingly, a damage threshold for excitation light is high, and higher power terahertz wave can be generated. Further, according to another aspect of the present invention, large-scale equipment which is necessary for the production of a crystal using the melt method is not required, which allows providing a quality BNA crystal by a simple process. Furthermore, the energy expended on crystal production can be significantly reduced.

MODES FOR CARRYING OUT THE INVENTION

Figure 1:
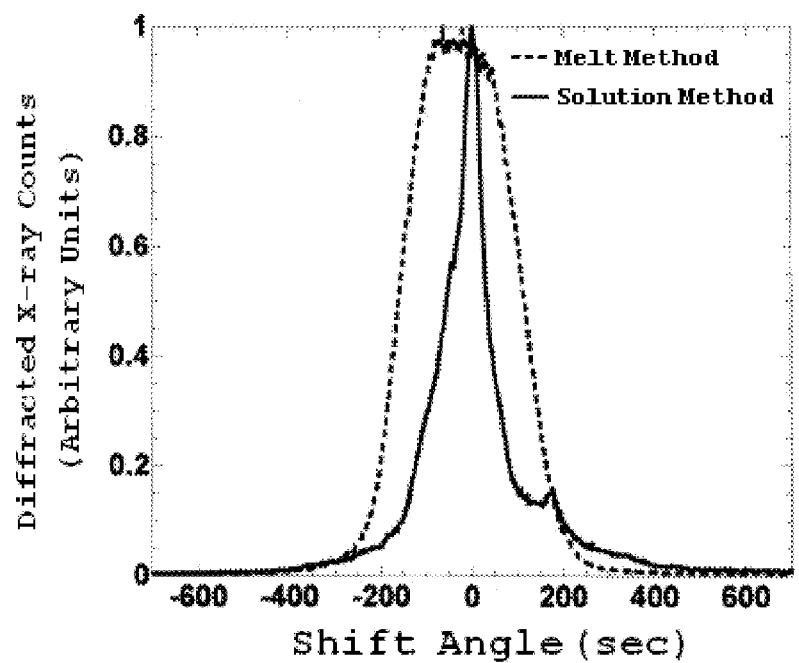
FIG. 1 is a graph showing the results of rocking curve measurements by X-ray diffraction method with respect to the BNA crystal of the present invention and a BNA crystal produced by the melt method.

The BNA crystal of the present invention is a BNA crystal characterized by having a half-value width of diffraction peak X-ray intensity of 100 seconds or less in a rocking curve measurement by X-ray diffraction method.

BNA is an organic nonlinear optical crystal using a material of 4-nitroaniline type. BNA is excellent in chemical stability of a crystal and has no deliquescence, and therefore does not undergo deterioration over time even when used in a normal environment. Thus, a quality BNA single crystal is expected to find application in the market as a next-generation broadband terahertz wave generating element, an electric field sensor, an ultra-high-speed light modulation/switching element, and the like.

The BNA crystal of the present invention has a half-value width of diffraction peak X-ray intensity of 100 seconds or less in a rocking curve measurement by X-ray diffraction method, which is a physical property that conventional BNA crystals do not have.

The rocking curve by X-ray diffraction method is an intensity distribution curve of diffracted X-rays obtained by applying X-rays to a single crystal from a given direction, fixing the detector angle under conditions satisfying the Bragg condition, and slightly shifting only the X-ray incidence angle. The measurement of a rocking curve is convenient because it does not require any particular treatment of samples before measurement and is a nondisruptive measurement. Generally, variations of crystal orientation and crystal plane index are evaluated using the rocking curve measurement by X-ray diffraction method. Specifically, when a crystal is in the ideal state, the rocking curve measurement shows a sharp peak. Therefore, a BNA crystal showing a sharp peak with a narrow half-value width can be assumed to be in a near-ideal crystal state.

The rocking curve by X-ray diffraction method can be measured using a common commercially available X-ray diffraction apparatus. The wavelength of X-rays during measurement is not particularly restricted because the measurement results do not vary depending on the wavelength of X-rays. For example, as in Examples, CuKα radiation at a wavelength of 1.54 Å can be employed.

The BNA crystals hitherto known which are produced by the melt method have a half-value width of diffraction peak X-ray intensity of about 200 seconds in the rocking curve measurement described above (see FIG. 1), and those skilled in the art will readily appreciate that the quality difference compared to the BNA crystal of the present invention is obvious.

The BNA crystal of the present invention preferably has a half-value width of diffraction peak X-ray intensity of 90 seconds or less, more preferably 85 seconds or less, and still more preferably 75 seconds or less, in the rocking curve measurement described above. It is evident from common technical knowledge that the half-value width is preferably as narrow as possible and the lower limit is not particularly limited.

A method for the BNA crystal of the present invention to achieve a half-value width of diffraction peak X-ray intensity of 100 seconds or less in the rocking curve measurement described above is shown below.

First, BNA crystals produced by the melt method such as the vertical Bridgman method, as previously mentioned, have the advantage that a large single crystal can be grown, but on the other hand require a large temperature gradient at a growth interface in order to crystallize a melt and also undergo mechanical stress caused by the difference in thermal expansion between a crystal and an ampule for containing it. As a result, lattice distortion is likely to occur in the crystals, and defect density tends to be high. Thus, it is preferable to produce a BNA crystal by the solution method.

In the solution method, although a solution used is an organic solvent, a higher-quality BNA crystal can be obtained by using alcohol, and using, in particular, ethanol is preferred for obtaining a high-quality BNA crystal.

In addition, to prepare a seed crystal, using a high-purity BNA as a raw material is preferred for obtaining a high-quality BNA crystal, and when precipitating a seed crystal and when growing the seed crystal, employing slow cooling is preferred for obtaining a high-quality BNA crystal.

Further, when growing the seed crystal, using a supernatant solution after precipitation of the seed crystal as a solution for growing the seed crystal is preferred for obtaining a high-quality crystal. Furthermore, growing the crystal in such a manner that the direction of the growth of the seed crystal is taken into consideration is also preferred for obtaining a large and high-quality crystal.

In Patent Document 1, the seed crystal generated moves downward due to inclination, is held by a groove arranged, and grows. However, the inventors have discovered that to produce a high-quality and large crystal in BNA crystals, the direction of its growth is very important. Thus, growing the crystal in such a manner that the direction of the growth of the crystal is taken into consideration is preferred for obtaining a large and high-quality BNA single crystal.

The BNA crystal of the present invention is characterized also by being large in addition to being of high quality as described above. Specifically, it is preferable to have a long side/short side length of 5 mm or more and a thickness of 0.5 mm or more. The long side of the BNA crystal of the present invention represents the length of the longest direction of the three directions of a rectangular parallelepiped shape, and the short side represents the length of the second longest direction of the three directions. The thickness is the length of the direction perpendicular to the surface comprising the long side and short side described above. The BNA crystal of the present invention is a high-quality and large crystal and expected to be put to practical use as an organic nonlinear optical crystal for high-power terahertz-wave generation. The BNA crystal of the present invention more preferably has a long side of 5 mm or more, still more preferably 10 mm or more, particularly preferably 12 mm or more, and most preferably 15 mm or more. The short side is more preferably 5 mm or more and still more preferably 8 mm or more.

The BNA crystal of the present invention is not only of high quality but also has excellent durability to light intensity. Specifically, the damage peak power density (damage threshold) for Nd:YAG excitation light at a 1064 nm is 20 MW/cm$^2$ or more. When damage occurs in a wavelength conversion crystal upon irradiation with light having a peak power density over a certain value, the value is called the damage peak power density (damage threshold), the higher value indicating being highly durable and practical. The value is preferably 22 MW/cm$^2$ or more and more preferably 24 MW/cm$^2$ or more.

The method for measuring a damage peak power density is as follows:

First, since the absorption edge of BNA crystals is present near 470 nm, excitation light at a wavelength longer than 470 nm is required. In addition, from the phase-matching condition for terahertz generation, it has become clear that a suitable excitation wavelength range is in the vicinity of 1000 nm. Accordingly, a Nd:YAG laser system with a fundamental wave at a wavelength of 1064 nm was used in measuring a damage peak power density for excitation light.

The oscillation pulse width of the laser used in the measurement is 6 ns, and the repetition is 100 Hz. The sample irradiation time is 1 minute, and the beam diameter is about 1 mm. By changing the energy of the laser, the peak power density of impingement on the crystal is changed stepwise in increments of about 1 MW/cm$^2$. At the end of the measurements at each peak power density value, a crystal surface is observed using a light microscope to check whether the surface is damaged. If there is no damage, the energy is increased stepwise to carry out a similar irradiation test, and the evaluation is repeated. The peak power density value measured when damage is observed is defined as the damage peak power density.

The process for producing the BNA crystal of the present invention will now be described.

The BNA crystal of the present invention is preferably produced by the solution method. BNA crystals obtained by the melt method, although already known, are large but have low crystal quality as described previously. Thus, in the present invention, it is preferable to produce a BNA crystal by the solution method.

Although the solution method is a method known in the field of crystal production, there are no reports of the production of a high-quality and large BNA crystal using the solution method. The present inventors believe this fact as follows:

BNA has a crystalline nucleus with a large critical nucleus radius, and the degree of supersaturation of a saturated solution is extremely high. Thus, it is considered that it has been extremely difficult to precipitate a crystal moderately and control the growth rate of the crystal only by cooling the saturated solution. In such a high supersaturation, it is difficult to precipitate a moderate crystal, but on the other hand once a crystal starts to precipitate in a solution for some reason, the driving force for crystal growth of the solution becomes extremely high, causing problems such as mass generation of microcrystals, needle-shaped crystals, and polycrystallization due to a number of precipitated crystals adhering to each other.

For these reasons, it is considered that the present invention was not conceivable simply by applying the known solution method in producing a BNA crystal. Now, the process for producing the BNA crystal of the present invention using the solution method, a preferred aspect, will be described.

The crystal production process using the solution method is broadly divided into two steps: the step of obtaining a seed crystal and the step of growing the seed crystal. First, examples of the step of obtaining a seed crystal include a method in which BNA raw material is dissolved in a solution and a crystal is precipitated by decreasing the temperature to obtain a seed crystal.

<The Step of Obtaining a Seed Crystal>

As a solvent used in the solution method, an organic solvent is commonly used. The type of the organic solvent is appropriately selected depending on the target compound to be crystallized, and in the case of a BNA crystal, it is preferable to use an alcohol solvent from the standpoint of solubility; it is more preferable to use a $C_1$-$C_4$ lower alcohol; and it is still more preferable to use ethanol. It is preferable to use ethanol, which has appropriate solubility, because the degree of supersaturation of a saturated solution of BNA is extremely high.

When using the alcohol solvent described above, it can be used in mixture with other solvents such as water, but the alcohol purity is preferably high. The concentration of the alcohol solvent is preferably 70% by weight or more, more preferably 80% by weight or more, still more preferably 90% by weight or more, and particularly preferably 95% by weight or more, and an alcohol of infinitely high purity is most preferred. An alcohol solvent containing a plurality of alcohols may also be used.

The BNA raw material used in the crystal production can be obtained by performing organic synthesis using the method described, for example, in Hashimoto et al. (1997) Jpn. J. Appl. Phys. Vol. 36, Pt. 1, No. 11.

As a BNA raw material, it is preferable to use high-purity one from the standpoint of crystal quality. To increase purity, known purification processes such as recrystallization, extraction, and distillation can be used. To increase purity, purification is preferably performed more than once; in particular, in the case of extraction and distillation, it is preferable to perform the purification five times or more, and in the case of recrystallization, it is preferable to perform the purification ten times or more. The purity of the raw material in the process for producing a BNA crystal is preferably 2 N or more, more preferably 3 N or more, and still more preferably 4 N or more.

Precipitation of a seed crystal using the solution method can be carried out by cooling a BNA solution obtained by dissolving the BNA raw material described above in a solvent. Specifically, the temperature of a solvent is increased to prepare a highly-concentrated BNA solution, which is cooled to allow precipitation of a seed crystal. The temperature of the solvent for dissolving the BNA raw material is preferably 40° C. to 80° C., more preferably 45° C. to 75° C., and still more preferably 50° C. to 70° C. Although the cooling rate is not particularly restricted and can be set as appropriate, generally, the cooling rate may be about 0.02 to 0.15° C./hr.

Alternatively, a seed crystal can also be precipitated by preparing a low-concentrated solution without increasing the temperature of a solution so high and cooling the solution. The temperature of the solvent in this case is preferably 5° C. to 40° C., more preferably 10° C. to 35° C., and still more preferably 15° C. to 30° C. When a seed crystal is precipitated from a low-concentrated solution, it is preferable to employ slow cooling, and the rate of slow cooling is preferably 3° C./day or less, more preferably 1.5° C./day or less, and still more preferably 0.5° C./day or less. Because the slower the rate of slow cooling described above, the more time it takes to precipitate a crystal, it generally takes about 5 days to 20 days to precipitate a crystal, but the slower the rate of slow cooling, the more effective it is for inhibiting the generation of microcrystals and polycrystallization.

Generally, it is difficult to control the number or position of crystals to be generated by a method of precipitating a crystal by cooling a solution using the solution method. Thus, using the method described above, a plurality of seed crystals probably precipitate in a solution, and it is preferable to select a crystal of highest quality at this time point and eliminate the other crystals from the solution.

The seed crystal thus obtained has a long side/short side length of up to about 3 mm and a thickness of up to about 0.2 mm, and used as a seed crystal in the following crystal growth step.

<The Crystal Growth Step>

The crystal growth step of the present invention is a step for growing the seed crystal obtained above in a solution.

The seed crystal obtained is allowed to stand in a BNA solution again to grow the crystal. Although the BNA solution used here can be used with its concentration being adjusted as appropriate, the present inventors have discovered that the determination of the concentration is important because when the concentration is too high, microcrystals are highly likely to precipitate, and when it is too low, a crystal does not grow sufficiently, and besides the seed crystal dissolves. Then, the present inventors conceived that a high-quality and large BNA crystal can be obtained by the solution method by using a supernatant solution of the solution after precipitation of the seed crystal in the above-described step of obtaining a seed crystal. The supernatant solution refers to a filtrate obtained after selecting the seed crystal when the seed crystal described above precipitated and carrying out filtration in order to eliminate the other crystals from the solution.

In the supernatant solution after seed crystal precipitation, the degree of supersaturation has been reduced because BNA crystals have already precipitated, and microcrystals or a large amount of crystals are probably less likely to further precipitate. Further, since the other superfluous precipitated crystals have been eliminated, nutrients in the solution will be supplied concentratedly to the desired seed crystal to be grown, and the seed crystal can be grown with efficiency. In addition, there is no need to prepare another solution for growth, which simplifies the production process.

Further, by using the above-described supernatant solution after seed crystal precipitation, the seed crystal will not dissolve, and a quality crystal can be grown. It should be understood that those skilled in the art can appreciate that although growing a crystal in the supernatant solution after seed crystal precipitation is a preferred aspect, a solution of similar BNA concentration prepared by measuring electrical conductivity of a solution without using this method can also be used as a solution for crystal growth, and therefore the use of the supernatant solution after seed crystal precipitation is not the only method for producing the high-quality BNA crystal of the present invention.

The seed crystal obtained, which will be grown in the BNA solution, is held by a crystal holding part in the BNA solution. The crystal holding part is capable of holding the crystal, and, for example, the material, size, and shape thereof are not restricted as long as it does not readily react with an organic solvent. Examples of the material include, for example, glass plate and the like; the size may be any size as long as it is large enough to hold the crystal and fits into a container to be filled with the solution; and examples of the shape include a cylindrical, prismatic, plate-like, film-like, and the like.

The seed crystal held by the crystal holding part described above is preferably held by the holding part at the end in the main growth direction of the seed crystal. According to such a holding method, in the step of growing the BNA crystal, a high-quality crystal can be obtained by taking the growth direction of the crystal into consideration so as not to inhibit the growth of the crystal. The main growth direction of the crystal herein refers to the direction in which the crystal is most likely to grow. An a-axis, b-axis, and c-axis direction, fundamental vectors that represent three edges forming a unit cell of a BNA crystal that belongs to the orthorhombic system, and the main growth direction have a relationship such that the main growth direction exists in the direction forming an angle of about 45° with the a-axis and c-axis and about 90° with the b-axis. In the case of an orthorhombic crystal, the a-axis, b-axis, and c-axis perpendicularly intersect one another. The main growth direction of the crystal can be determined by comparing the seed crystal with the crystal form after growth. Further, the crystallographic axis direction can be determined by X-ray diffraction structural analysis and terahertz generation test. The end in the main growth direction means a part from one end within one third, preferably one fourth, and more preferably one fifth of the length in the main growth direction of the crystal. When the seed crystal is held by the holding part at the end in the main growth direction of the crystal, inhibition in the growth direction of the crystal is reduced, and a large and good quality crystal is readily obtained.

Although the method of holding the seed crystal by the crystal holding part described above is not particularly limited, from the standpoint of crystal growth inhibition, preferred is holding by adhesive fixation to the crystal holding part on one surface located substantially parallel to the main growth direction of the seed crystal. Because the BNA seed crystal is small, it is quite difficult to sandwich it with a plurality of crystal holding parts, and when holding the BNA seed crystal by placing it on a support, the contacting surface between the crystal and the support is large and subject to mechanical stress.

Although the adhesive for adhering the crystal to the crystal holding part described above is not particularly limited, it is preferable to use an instant adhesive for glass.

The position for holding the seed crystal in a solution is preferably located at the upper part in the solution in order to prevent polycrystallization due to binding of the seed crystal to a possible deposit of the precipitated crystal at the bottom of the solution. Further, to prevent adverse effects of the contact of the adhesive with the solution on the solution, dissolution of the adhesive due to an organic solvent, and the like, it is preferred that the solution have a liquid level lower than the part where the seed crystal and the crystal holding part are fixed such that the adhesive and the liquid level are not in contact.

Figure 2:
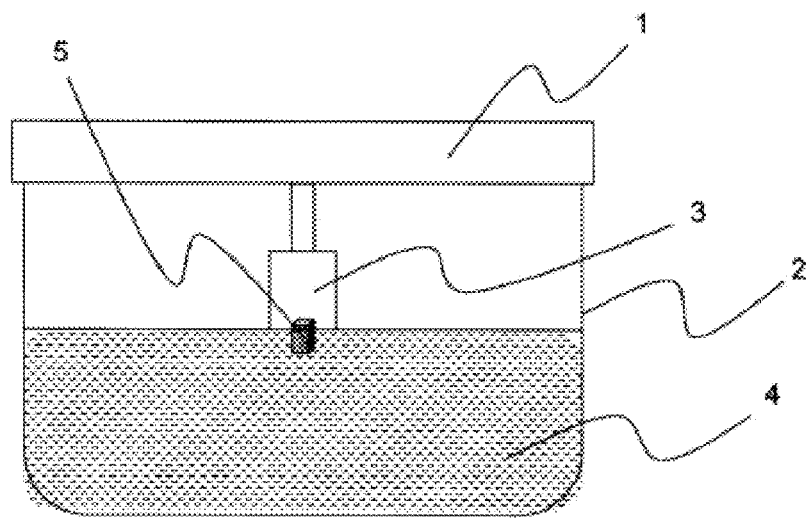
FIG. 2 is a schematic view illustrating an aspect of the crystal growth step of the present invention.
Figure 3:
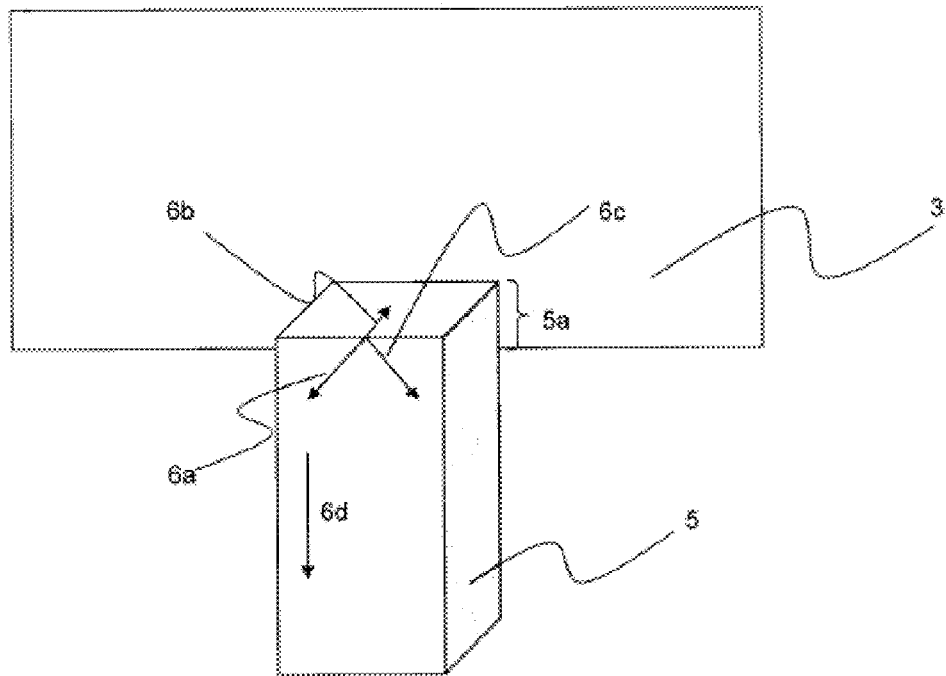
FIG. 3 is a schematic view illustrating an aspect in which a seed crystal is held among the aspects of the crystal growth step of the present invention.

FIG. 2 and FIG. 3 show aspects of the crystal growth step of the present invention. In FIG. 2, a seed crystal 5 is placed in a container and hung from above by the crystal holding part. FIG. 3 is an enlarged view of the part where the seed crystal 5 and the crystal holding part 3 are fixed; the main growth direction of the crystal, in which direction the BNA seed crystal 5 has the largest growth rate, is 6d, and there are four surfaces that are present parallel to the main growth direction of the crystal. On one of the surfaces, the seed crystal 5 is fixed to the crystal holding part. In the BNA seed crystal 5, the end in the main growth direction of the crystal is 5a, and by such fixation to the crystal holding part at the end of the main growth direction of the crystal, inhibition of crystal growth is reduced, whereby a quality crystal can be grown.

As described above, the seed crystal is held in the BNA solution to grow the crystal. For high-quality crystal growth, slow cooling is preferred here again. The rate of slow cooling is preferably 3° C./day or less, more preferably 1.5° C./day or less, and still more preferably 0.5° C./day or less. Because the slower the rate of slow cooling described above, the more time it takes to grow the crystal, it generally takes about 10 days to 50 days to grow the crystal, but the slower the rate of slow cooling, the more effective it is for higher quality and for inhibiting the generation of microcrystals and polycrystallization.

It should be understood that the process for producing the BNA crystal of the present invention is applicable to other organic compounds. Generally, most of the organic compounds are thermally unstable and pyrolyze at or lower than their melting point, and it is difficult to apply the melt growth method to such organic compounds. The production process of the present invention allows crystal growth at a temperature much lower than the melting point, thus the growth of a high-quality crystal can be expected when applied to an organic compound with a particularly low melting point. Specifically, it is suitable for the process for producing an organic compound with a melting point of 200° C. or less and preferably a melting point of 150° C. or less. Further, it is suitable for the process for producing an organic compound that pyrolyzes at 200° C. or less and preferably 150° C. or less. For the pyrolysis described above, the pyrolysis is considered to have occurred at the time point when the organic compound has undergone structural change due to heat.

Examples

The present invention will now be described in more details by way of Examples, but, needless to say, the present invention is not limited to these Examples.

<Preparation of High-Purity BNA Raw Material>

Using MNA (2-methyl-4-nitroaniline) and Benzyl bromide as raw materials, organic synthesis of the process for producing a BNA crystal was performed according to the procedure disclosed in Hashimoto et al. (1997) Jpn. J. Appl. Phys. Vol. 36, Pt. 1, No. 11. For the BNA raw material obtained, recrystallization was carried out for ten times using an enol solution to obtain a high-purity BNA raw material.

<Precipitation of Seed Crystal>

The high-purity BNA raw material obtained was dissolved in ethanol to prepare a high-purity-BNA-containing ethanol solution at 20° C., which was slowly cooled at a rate of 0.5° C./day. Although crystals started to precipitate in about two weeks, the slow cooling was continued until the temperature of the solution reached 0° C.

Among the crystals precipitated upon slow cooling, the crystal that appeared to be of highest-quality was selected as a seed crystal. The selection of the seed crystal was carried out by judging transparency, the presence of linear defects, shape of the crystal, and the like as a whole, and for the size, one having a size of about 3 mm×2 mm×0.3 mm is finally obtained. The other precipitated crystals were removed by filtration to obtain a supernatant solution.

<Growth of Seed Crystal>

As shown in FIG. 2, the seed crystal was stuck to a glass plate. The adhesive used is a commercially available instant adhesive for glass. The length of the seed crystal in the main growth direction was 3 mm, and the seed crystal was fixed to the glass plate at the upper end 1 mm portion. The supernatant solution obtained was poured into a beaker to the extent that the glass plate was marginally soaked, and, as a result, about 2 mm from the bottom of the seed crystal was impregnated into the supernatant solution.

Figure 4:
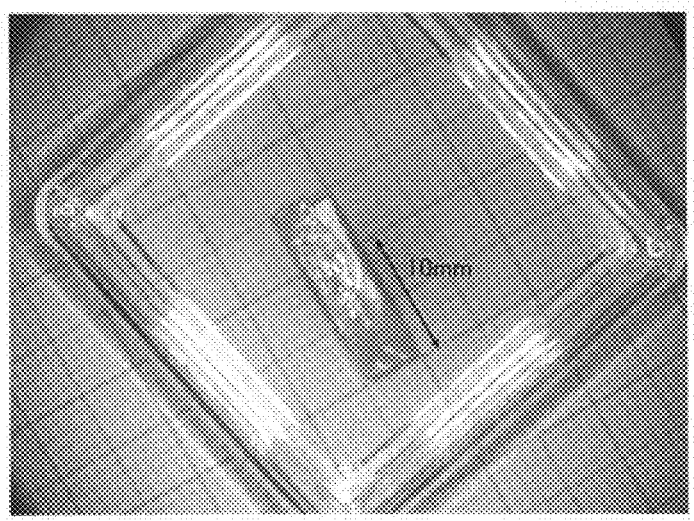
FIG. 4 is a BNA crystal provided by the present invention (photograph)

Then, the beaker into which the supernatant solution obtained in the precipitation of the seed crystal was poured was slowly cooled again at a rate of 0.5° C./day. The temperature of the solution at the beginning of the slow cooling is 18° C. After 30 days, a crystal 1 of 15 mm×5 mm×0.6 mm was obtained. FIG. 4 shows a photograph of the crystal 1.

<Evaluation of Crystal Quality>

For the crystal 1 obtained and a crystal 2 obtained by the melt method, rocking curve measurements were made using X-ray diffraction method. The measurement method is as described below. The results are shown in FIG. 1. Measurement Method Using a commercially available X-ray diffraction apparatus (manufactured by Philips), X-ray diffraction rocking curve measurements from the (010) surface of a BNA crystal were made. The wavelength used is CuKα radiation at a wavelength of 1.54 Å.

<Evaluation of Crystal Durability>

Figure 5:
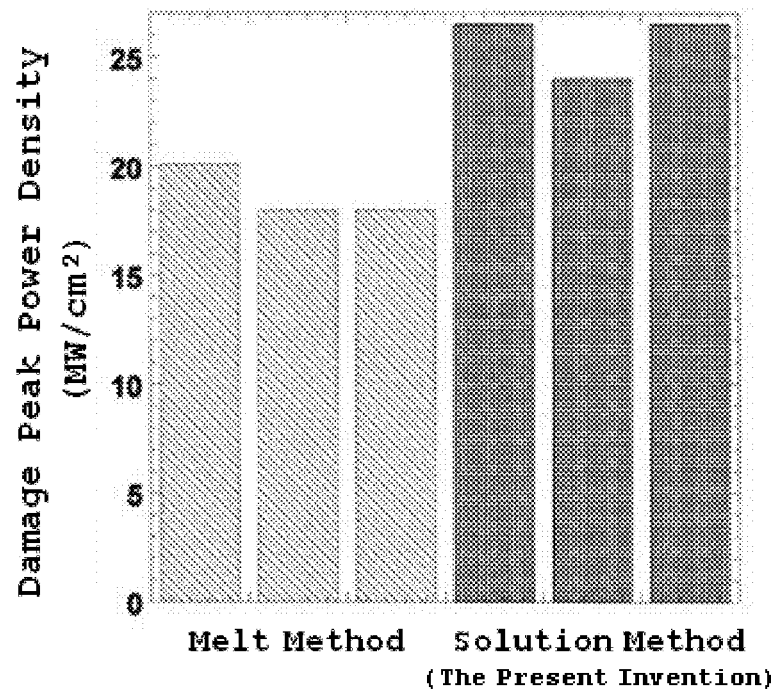
FIG. 5 is a graph showing the results of measurements of damage peak power density with respect to the BNA crystal of the present invention and a BNA crystal produced by the melt method.

For the crystal 1 obtained and the crystal 2 obtained by the melt method, damage peak power density were measured. The measurement method is as described below. The results are shown in FIG. 5. Measurement method: As a light source, a Nd:YAG laser system (available from SOLAR) at a wavelength of 1064 nm was used. The oscillation pulse width of the laser is 6 nm, and the repetition is 100 Hz. The sample irradiation time is 1 minute, and the beam diameter is about 1 mm.

As is evident from the evaluation of crystal quality described above, the quality of the BNA crystal of the present invention is distinctly different from that of conventional BNA crystals. Until now, there has not been such a BNA crystal. Further, as is evident from the evaluation of crystal durability described above, the durability has also improved compared to conventional BNA crystals.

DESCRIPTION OF SYMBOLS

1: Lid
2: Beaker
3: Crystal holding part
4: BNA solution
5: BNA crystal
5a: End of BNA crystal
6a: a-axis
6b: b-axis
6c: c-axis
6d: Main growth direction

The invention claimed is:

1. A BNA crystal having a half-value width of diffraction peak X-ray intensity of 100 seconds or less in a rocking curve measurement by X-ray diffraction method, wherein the crystal is produced by a solution method comprising a step of obtaining a seed crystal and a step of growing the crystal from the seed crystal in a solution,
wherein
the seed crystal is held by a crystal holding part at an end in the main growth direction of the seed crystal, and
the solution is a supernatant solution after precipitation of the seed crystal in the step of obtaining the seed crystal.

2. The BNA crystal according to claim 1, having a long side of 5 mm or more, a short side of 5 mm or more, and a thickness of 0.5 mm or more.

3. The BNA crystal according to claim 1, wherein the crystal is precipitated and grown by slowly cooling the solution in the step of obtaining the seed crystal and/or the step of growing the crystal.

4. A process for producing a BNA crystal by a solution method, comprising a step of obtaining a seed crystal and a step of growing the crystal from the seed crystal in a solution,
wherein, in the step of growing the crystal, the seed crystal is held by a crystal holding part at an end in the main growth direction of the seed crystal, and
the solution used in the step of growing the crystal is a supernatant solution after precipitation of the seed crystal in the step of obtaining the seed crystal,
thereby providing a BNA crystal having a half-value width of diffraction peak X-ray intensity of 100 seconds or less in a rocking curve measurement by X-ray diffraction method.

5. The process for producing a BNA crystal according to claim 4, wherein the crystal is precipitated and grown by slowly cooling the solution in the step of obtaining the seed crystal and/or the step of growing the crystal.

* * * * *